(12) United States Patent
Skerven et al.

(10) Patent No.: US 8,187,172 B2
(45) Date of Patent: May 29, 2012

(54) ENDOSCOPE CAP WITH APERTURE

(75) Inventors: Gregory J. Skerven, Kernersville, NC (US); John A. Karpiel, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 806 days.

(21) Appl. No.: 12/250,287

(22) Filed: Oct. 13, 2008

(65) Prior Publication Data

US 2009/0105539 A1    Apr. 23, 2009

Related U.S. Application Data

(60) Provisional application No. 60/981,610, filed on Oct. 22, 2007.

(51) Int. Cl.
*A61B 1/00* (2006.01)
(52) U.S. Cl. .......................... 600/114; 600/127; 600/129
(58) Field of Classification Search ................. 600/127, 600/129
See application file for complete search history.

(56) References Cited

U.S. PATENT DOCUMENTS

| | | | | |
|---|---|---|---|---|
| 5,263,928 A * | 11/1993 | Trauthen et al. | ............ | 604/509 |
| 5,908,427 A * | 6/1999 | McKean et al. | ............... | 606/139 |
| 6,059,719 A * | 5/2000 | Yamamoto et al. | ........... | 600/127 |
| 6,979,290 B2 * | 12/2005 | Mourlas et al. | ............ | 600/115 |
| 7,331,975 B2 * | 2/2008 | Yanuma et al. | ............... | 606/200 |
| 7,775,968 B2 * | 8/2010 | Mathis | ............ | 600/104 |
| 2003/0009085 A1 * | 1/2003 | Arai et al. | ................... | 600/127 |
| 2003/0114732 A1 | 6/2003 | Webler et al. | | |
| 2003/0225312 A1 * | 12/2003 | Suzuki et al. | ................ | 600/114 |
| 2004/0034278 A1 * | 2/2004 | Adams | ........................ | 600/127 |
| 2004/0082832 A1 | 4/2004 | Moriyama | | |
| 2005/0165272 A1 * | 7/2005 | Okada et al. | ................ | 600/114 |
| 2005/0288549 A1 * | 12/2005 | Mathis | ........................ | 600/104 |
| 2006/0229496 A1 | 10/2006 | Windheuser et al. | | |

FOREIGN PATENT DOCUMENTS

| | | | |
|---|---|---|---|
| EP | 1442716 A1 | | 8/2004 |
| JP | 59-93413 | * | 5/1984 |
| WO | WO 01/58360 A2 | | 8/2001 |

* cited by examiner

*Primary Examiner* — Matthew J Kasztejna
(74) *Attorney, Agent, or Firm* — Brinks Hofer Gilson & Lione

(57) ABSTRACT

An end cap for an endoscope. The end cap is configured to allow the endoscope to be introduced into a patient body by a short-wire type of operation.

3 Claims, 3 Drawing Sheets

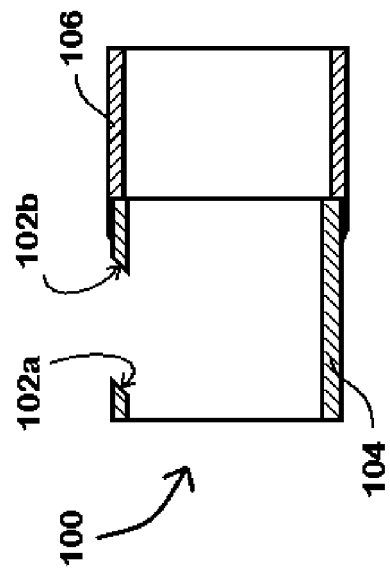
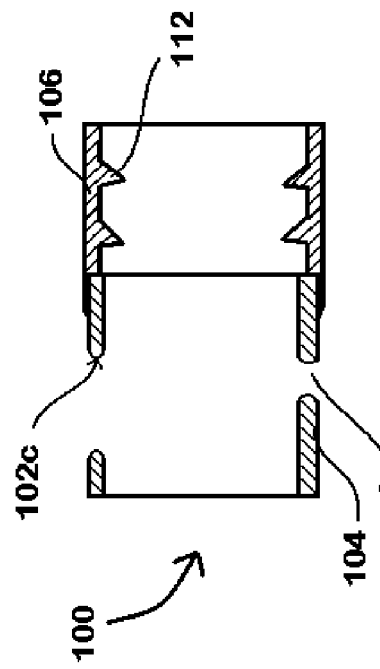
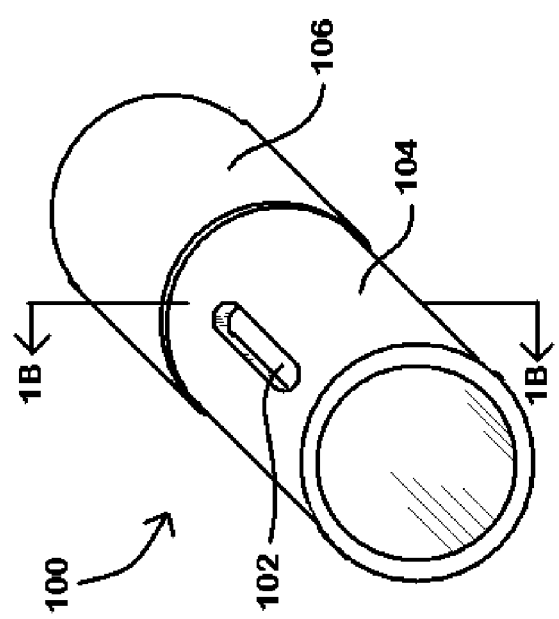

ENDOSCOPE CAP WITH APERTURE

CROSS-REFERENCE TO RELATED APPLICATIONS

This application claims priority to U.S. Provisional Application Ser. No. 60/981,610, filed Oct. 22, 2007, which is incorporated herein by reference in its entirety.

FIELD OF THE INVENTION

The present invention relates generally to medical devices and specifically to an accessory for an endoscope.

BACKGROUND

Endoscopes are well-known in the art of minimally invasive surgery for the observation of, and introduction of materials and devices to, sites inside a patient's body. For example, catheter-based devices are commonly introduced through a working channel (also known as "accessory channel") of an endoscope to a site in a patient's body. A well-established technique, known as "long wire guide," is commonly used for guiding a delivery catheter to a target site in a patient's body and it includes: (1) directing a steerable wire guide through a working channel to the target site; (2) retaining a proximal portion of the wire guide outside the body; (3) threading a delivery catheter, which has a wire guide lumen throughout its length, onto the proximal end of the wire guide; and (4) advancing the catheter along the wire guide to the treatment site.

One example of a desired path to a target site is the passage through a working lumen or channel of an endoscope to a biliary duct or another structure along the alimentary canal in a gastroenterological application. The catheter device may include a treatment device such as a stent or fluid-inflatable balloon disposed at its distal end for deployment at a target site (e.g., an occluded biliary duct or coronary artery). The catheter may also have a tool such as a cutting wire or cutting needle disposed at or near its distal end (e.g., a papillotome, sphincterotome, etc.), or the catheter may have an aperture for the delivery of a fluid through a second lumen (e.g., radio-opaque fluid for contrast fluoroscopy, adhesive or gelling agent for delivery to a target site, etc.).

Procedures that employ wire guides may require exchange of treatment appliances. For example, a balloon catheter may be replaced with a stent deployment catheter. In a typical application of such a procedure, a balloon catheter is directed to the site of a stenosis (e.g. in an artery, biliary duct, or other body lumen) as described above. Fluid is then used to inflate the balloon so as to dilate the stenosis. Some procedures are effectively concluded at this point. However, many procedures follow dilation of the stenotic stricture with the placement of a stent to maintain patency of the reopened lumen. This may require that the balloon catheter be withdrawn to allow for the introduction of a stent-deployment catheter (unless a stent placement catheter with an internal/placement balloon is used to accomplish both stenosis-dilation and stent-placement). It is preferable that the wire guide remain in place for guidance of the stent-deployment catheter without having to re-navigate the wire guide back into to the newly reopened lumen.

In order to prevent undesired displacement of the wire guide, any exchange of long wire guide catheters requires that the proximal portion of the wire guide extending out of the patient's body (or endoscope, depending on the entry point for the desired path to the target site) be longer than the catheter being "exchanged out," so that control of the wire guide may be maintained as the catheter is being removed. Likewise, the wire guide must be grasped while the entire catheter being "exchanged in" is threaded onto it and directed along the desired path to the target site. In other words, for the operating physician and assistant to be able to hold the wire guide in place while removing one catheter for replacement with another, each of the catheters must be shorter than the portion of the wire guide that is exposed outside the patient's body (and, if used, outside the endoscope). Put another way, the wire guide must be about twice as long as a catheter that is being used over that wire guide. Additionally, in the case of gastrointestinal endoscopy, even more wire guide length is necessary. This is because the shaft of the endoscope through which the wire guide and catheters are placed must have a length outside the body for manipulation and control, and the catheter itself must have some additional length outside of the endoscope for the same reason. As those skilled in the art will appreciate, wire guides having the necessary "exchange length" are cumbersome and difficult to prevent from becoming contaminated.

An alternative technique for guiding a delivery catheter to a target site in a patient body utilizes catheters having a relatively short wire guide lumen in catheter systems commonly referred to as "rapid exchange," "short wire guide," or "monorail" systems. In such systems, the wire guide lumen extends only from a first lumen opening spaced a short distance from the distal end of the catheter to a second lumen opening at or near the distal end of the catheter. As a result, the only lumenal contact between the catheter's wire guide lumen and the wire guide itself is the relatively short distance between the first and second lumen openings. Several known advantages are conferred by this configuration. For example, the portion of the wire guide outside the patient's body may be significantly shorter than that needed for the "long wire configuration." This is because only the wire guide lumen portion of the catheter is threaded onto the wire guide before directing the catheter through the desired path (e.g., a working lumen of an endoscope, an endoluminal passage, etc.) to the target site.

Similarly, during endoscopic procedures, there is sometimes a need to exchange the endoscope being used. For example, a physician may desire to exchange a side-viewing endoscope for an end-viewing endoscope, with the endoscope being "exchanged in" directed to a particular location where a wire guide or catheter device is already in place. Currently, such an exchange must be effected in a long-wire type of operation wherein, after the first endoscope is removed, the second endoscope is fed along the entire length of the wire guide or catheter device to the desired location, with that tracking through a working channel. As described above with reference to long-wire procedures as used with catheter devices, his maneuver requires that the wire guide or catheter device be very long (commonly >300 cm) so that the entire endoscope can be directed along it without losing the ability to hold onto at least one point of the wire guide or catheter device outside the patient's body. Such long devices pose difficulties in proper handling that prevents damage or contamination, sometimes requiring an extra person to hold the extra length.

Therefore, it would be advantageous to provide an endoscope and/or accessory thereto that would allow a user to utilize a short-wire type of operation, benefiting from the advantages of time and economy of motion presented thereby.

BRIEF SUMMARY

An end cap including a side aperture configured to function as a wire guide port may, in certain aspects, meet the needs of a physician desiring to exchange a endoscope using a short-wire type of operation. In one aspect, the present invention may include an end cap for a medical endoscope, which includes a generally tubular body having a proximal end portion and a distal end portion, and being open at both ends. The proximal end portion includes means for engaging a distal end of an endoscope, and the distal end portion includes at least one aperture configured to accommodate passage of a wire guide, with the aperture being disposed through a side wall portion of the distal end portion.

In another aspect, the present invention may include a method of introducing an endoscope using a short-wire operation. The method includes the steps of: providing an endoscope and a wire guide; providing an end cap; engaging the proximal end portion of the end cap to the distal end of the endoscope; directing a proximal end of the wire guide into a central region of the tubular body and out through the aperture; and advancing the endoscope and end cap distally along the wire guide. The end cap provided includes a generally tubular body having a proximal end portion and a distal end portion, and being open at both ends. The proximal end portion of the end cap is configured to engage a distal end of the endoscope; and the distal end portion includes at least one aperture configured to accommodate passage of the wire guide, with the aperture being disposed through a side wall portion of the distal end portion.

In yet another aspect the present invention may include an end cap for a medical endoscope. The end cap includes a generally tubular construction having a generally circular transverse cross-section open in its middle and including a proximal end portion and a distal end portion, with both ends being open to the middle. The proximal end portion includes a flexible material configured for being engaged around a distal end outer diameter of an endoscope, and the distal end portion includes a rigid material. Also, at least one elongate aperture configured to accommodate passage of a wire guide is disposed through the rigid material of the distal end portion.

BRIEF DESCRIPTION OF THE DRAWINGS

FIG. 1A depicts a perspective view of an end cap;

FIG. 1B shows a longitudinal section view of an end cap;

FIG. 1C illustrates a longitudinal section view of a different end cap embodiment;

DETAILED DESCRIPTION

Figure 2:
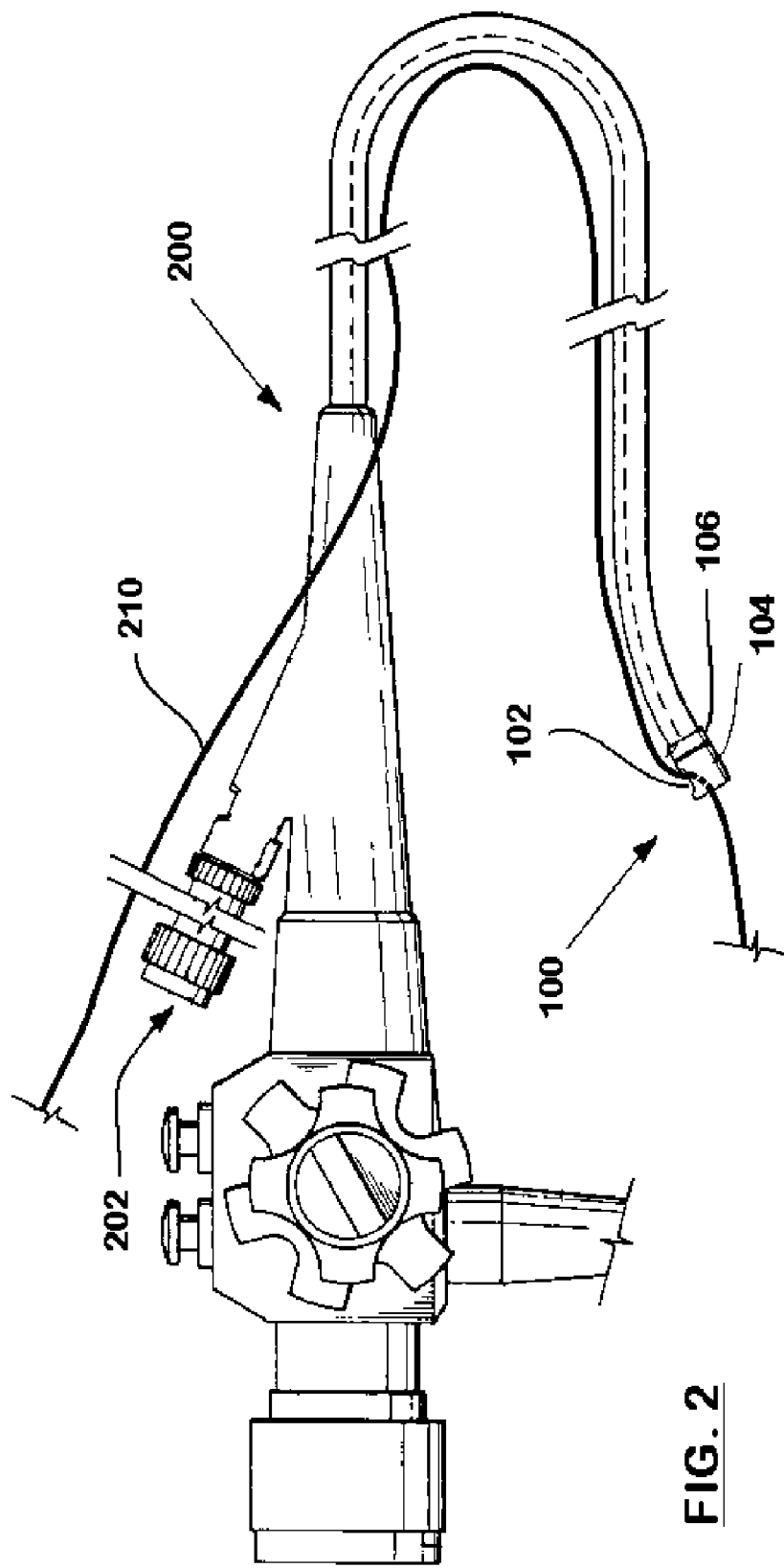
FIG. 2 shows an end cap placed onto an endoscope and disposed along a wire guide

An embodiment of an end cap 100 including a side aperture 102 is shown in FIGS. 1A-1C. FIG. 1A shows a perspective view of the end cap 100, and FIGS. 1B-1C show longitudinal section views of embodiments of the end cap 100 taken along line 1B-1B of FIG. 1A. The end cap 100 includes a generally tubular distal body portion 104 open at both ends, through which at least one side aperture 102 is disposed. The end cap 100 also includes a generally tubular proximal engagement portion 106.

The body 104 preferably is constructed of a rigid material, and the side wall of the body preferably is generally transparent. For example, in one embodiment, the body is constructed of a clear polycarbonate polymer, but it may be constructed of another clear, translucent, or opaque polymer such as polyurethane, acrylic, or nylon. The tubular construction of the body 104 preferably is dimensioned such that its outer diameter is about the same as the outer diameter of an endoscope on which the end cap 100 is to be used. For example the body 104 may have an outer diameter of about 8.5 mm to about 12 mm for use with endoscopes having those outer diameters, but those of skill in the art will appreciate that the body 104 may be dimensioned appropriately for use with endoscopes having greater or lesser diameters, and it may also have a non-circular cross-section for use with a similarly-shaped endoscope. The inner diameter preferably is configured such that, when the end cap 100 is used with an end-viewing endoscope, the end cap 100 does not significantly obscure the visual field of the endoscope (e.g., its camera, CCD, or fiber-optic element).

The engagement portion 106, which extends proximally from the body 104 preferably is constructed from a flexible material that provides a frictional inner diameter surface. For example, in one embodiment, the engagement portion is constructed of a clear polyurethane that is molded to the body 104. In other embodiments, it may be constructed from, for example, silicone or another soft polymer that will provide an ability to mount and frictionally (but removably) attach the end cap 100 to an endoscope. In the embodiment shown in FIG. 1C, the inner diameter of the engagement portion includes at least one groove, illustrated as a series of generally parallel grooves leaving a pair of engagement protrusions 112 having a generally right-triangular cross-section, and configured to aid in engagement by a barb-like or tooth-like function. In another embodiment, the grooves may have a different shape or pattern. The tubular construction of the engagement portion 106 preferably is dimensioned such that its outer diameter only slightly greater than the outer diameter of an endoscope on which the end cap 100 is to be used such that use of the end cap will not significantly increase the profile of the endoscope. Those of skill in the art will appreciate that the body 104 may be dimensioned appropriately for use with endoscopes having greater or lesser diameters than standard 8.5 mm to 12 mm endoscopes, and it may also have a non-circular cross-section for use with a similarly-shaped endoscope. The inner diameter preferably is configured such that engagement portion 106 of the end cap 100 will fit securely around an end portion of the outer diameter of an endoscope, as is described below with reference to FIG. 2.

In an alternative embodiment, the entire side cap may be constructed of a rigid material, with a means for attaching the proximal engagement portion to an endoscope. Such means could include an adhesive, an internal diameter surface configured to frictionally engage the endoscope, magnetic means, a threaded surface, a detent means, or other means as would be apparent in light of the present invention to one having skill in the art. In another alternative embodiment, an endoscope may include structure near its distal end for engaging the end cap such as, for example, complementary threaded surfaces, interlocking tabs/slots, or another connection means of a type presently known or developed in the future.

The body 104 includes a side aperture 102. The side aperture 102 preferably is elongate, having a generally obround or oval shape, the long axis of which preferably is generally parallel to a central longitudinal axis of the end cap 100. The side aperture 102 preferably is dimensioned to accommodate passage of a wire guide, but may also be configured to accommodate a larger-diameter item such as, for example, a catheter shaft. In one embodiment, the surface of the aperture 102 (where it intersects the wall of the body 104), may have its ends 102a, 102b each disposed at an angle as shown in FIGS. 1A-1B. The angle of end surface 102a is less than 90°, and the angle of end 102b is greater than 90°, each relative to the central longitudinal axis of the end cap. In some embodiments, the transition border 102c may be rounded between the aperture 102 and the inner and outer surfaces of the body, as is shown in a slightly different end cap embodiment in FIG. 1C, which also includes a second aperture 103 having a different shape than the first aperture 102. In other embodiments, more than one aperture may be included. In those or other embodiments, the aperture may have a different shape and/or size configured to accommodate different wire guides or other structures. The body 104 may be attached to the engagement portion 106 by adhesive, welding, mechanical fastener, or any other appropriate attachment means known to those of skill in the art.

FIG. 2 shows the end cap 100 in use with an endoscope 200. As illustrated, the end cap 100 is frictionally attached to the distal end of the endoscope 200. Specifically, the flexible engagement portion 106 of the end cap 100 is snugly fitted over the distal tip of the endoscope 200. The body 104 of the end cap 100 extends distally from the endoscope 100 in a manner that allows full operation of the endoscope's visualization, tool access, and other functions. The assembly of endoscope 200 and end cap 100 is shown as having been directed along a wire guide 210, which is disposed through the side aperture 102. In contrast with the prior art method of having to use a long wire guide to introduce a endoscope along a wire guide, the illustrated device allows for use of a shorter wire guide that can be grasped and controlled by a user without having to have been directed through the working channel 202 of the endoscope 200. In addition to allowing the advantageous use of a shorter wire, utilization of the end cap 100 also presents an advantage in having a lower frictional profile between the wire guide and endoscope than when the wire guide has to transit the entire length of the working channel.

Figures 3A, 3B:
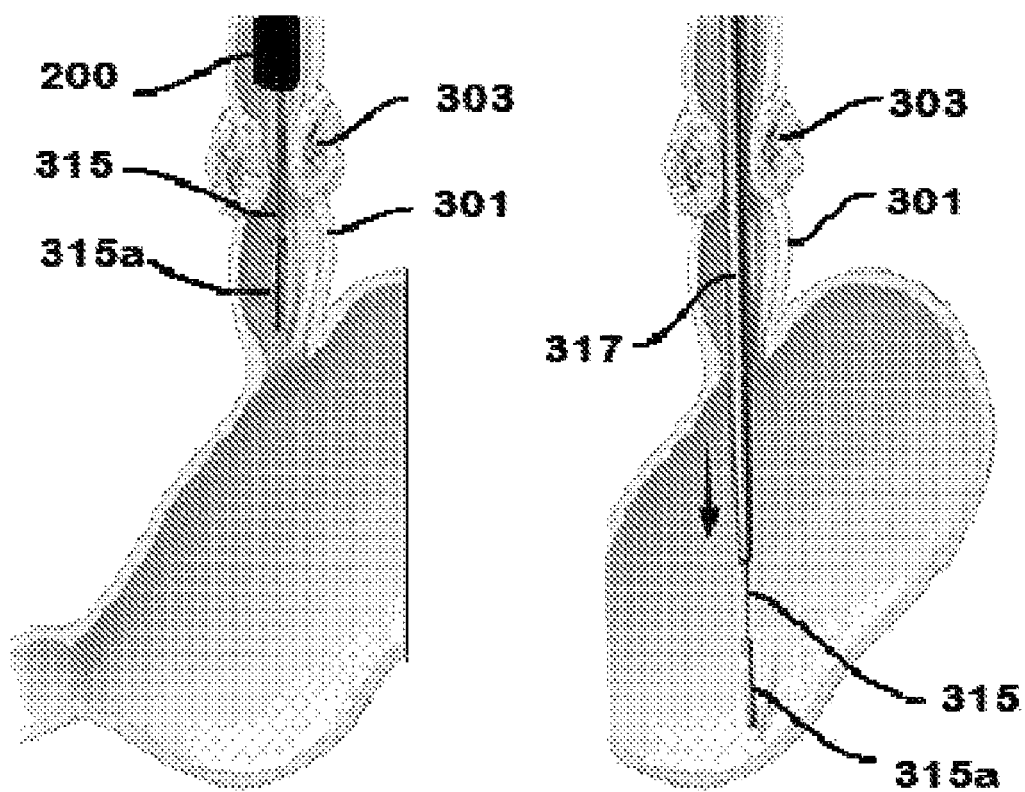
FIG. 3A depicts an endoscope in a patient esophagus, introducing a Savary wire guide.
FIG. 3B illustrates a Savary dilator in a patient esophagus.

One example of a procedure wherein an end cap of the present invention would be useful includes Savary esophageal dilation, which is illustrated with reference to FIGS. 2 and 3A-3B. This procedure is used to treat certain esophageal strictures. An endoscope 200 is directed down a patient's esophagus 301 to visualize a stricture 303, and facilitate placement of a Savary wire guide 315 proximate the stricture. The Savary wire guide 315 has a distal portion 315a with an outer diameter greater than that of the major length of the wire guide (which may function to keep dilators from going beyond a certain distal point along the wire guide). The endoscope 200 is withdrawn and a wire-guided Savary dilator 317 is introduced to dilate the stricture 303, typically with fluoroscopic visualization. In some instances a series of Savary dilators may be introduced and removed, with each one having a different (generally, successively greater) outer diameter to facilitate dilation of the stricture 303. At any point during the procedure, the physician may wish to view the patient's esophagus in a manner not provided for by fluoroscopy. In that event, the physician may place the end cap 100 onto the endoscope 200 in the same manner as described above and, after withdrawing the dilator 317, quickly navigate the endoscope in a short-wire operation along the wire guide 315 to the site that s/he wishes to view.

It should be appreciated that there are several different commercially-available models of endoscopes, and that minor modifications of end cap embodiments illustrated herein may be made to accommodate those endoscopes without departing from the endoscope of the present invention. Those of skill in the art will also appreciate that other embodiments not described explicitly herein may be practiced within the endoscope of the present invention. For example, an end cap may readily be configured for use with a side-viewing endoscope. It is therefore intended that the foregoing detailed description be regarded as illustrative rather than limiting, and that it be understood that the following claims, including all equivalents, are intended to define the spirit and endoscope of this invention.

We claim:

1. A method of performing a medical endoscope exchange, said method comprising steps of:
   directing a first endoscope to a target site within a patient body;
   directing a wire guide through a working channel of the first endoscope;
   withdrawing the first endoscope along the wire guide, leaving the wire guide in a desired location within the patient;
   providing an end cap that includes:
      a generally tubular body having a proximal engagement portion and a distal cap end portion, open at both ends;
      said distal end portion comprising at least one aperture configured to accommodate passage of the wire guide, said aperture disposed through a side wall portion of the distal end portion;
   attaching the proximal engagement portion of the end cap around a distal end of a second endoscope;
   directing a proximal end of the wire guide into the open distal end cap portion and out through the at least one aperture so that the wire guide extends along an external length of the second endoscope from the end cap toward a proximal end of the second endoscope; and
   navigating the second endoscope along the wire guide to a target location within the patient.

2. The method of claim 1, where the second endoscope is the same as the first endoscope.

3. The method of claim 1, further comprising a step of performing a therapeutic medical procedure after the step of withdrawing the first endoscope, and before the step of navigating the second endoscope.

* * * * *